US00PP26248P3

(12) United States Plant Patent
Fei et al.

(10) Patent No.: US PP26,248 P3
(45) Date of Patent: Dec. 22, 2015

(54) ***CAMELLIA* PLANT NAMED 'PINK CASCADE'**

(50) Latin Name: *Camellia L. hybrida*
Varietal Denomination: Pink Cascade

(71) Applicant: Shanghai Botanical Garden, The People's Republic Of China, Shanghai (CN)

(72) Inventors: Jian-Guo Fei, Shanghai (CN); Shu-Cheng Feng, Shanghai (CN); Ya-Li Zhang, Shanghai (CN); Jian-Bin Mo, Shanghai (CN)

(73) Assignee: Shanghai Botanical Garden, The People' Republic of China, Shanghai (CN)

( * ) Notice: Subject to any disclaimer, the term of this patent is extended or adjusted under 35 U.S.C. 154(b) by 83 days.

(21) Appl. No.: 13/986,736

(22) Filed: May 30, 2013

(65) Prior Publication Data

US 2013/0326780 P1 Dec. 5, 2013

(30) Foreign Application Priority Data

May 31, 2012 (CN) ..... 20120074

(51) Int. Cl.
*A01H 5/00* (2006.01)
*A01H 5/02* (2006.01)

(52) U.S. Cl.
USPC ..... Plt./244
CPC ... *A01H 5/00* (2013.01); *A01H 5/02* (2013.01)

(58) Field of Classification Search
USPC ..... Plt./243, 244
See application file for complete search history.

(56) References Cited

U.S. PATENT DOCUMENTS

PP21,687 P2 * 2/2011 Crocker ..... Plt./243

* cited by examiner

*Primary Examiner* — Susan McCormick Ewoldt
(74) *Attorney, Agent, or Firm* — Stites & Harbison PLLC; Richard S. Myers, Jr.

(57) ABSTRACT

A new and distinct *Camellia L.* plant named 'Pink Cascade', characterized by its lanceolate leave shape, the width of its leaves measuring at about 1.8 cm to about 2.2 cm, its cascade stem shape, its flower stage at early March to early April, its light pink flower color, its single flower shape, and its diameter of the flower measuring at about 2 cm to about 4 cm.

4 Drawing Sheets

Latin name of the genus and species of the plant claimed: *Camellia L. Hybrida.*

Variety denomination: 'Pink Cascade'.

RELATED APPLICATIONS

This application claims the benefit of People's Republic of China application for protection of new varieties plants in China Application Serial No. 20120074 filed on May 31, 2012 under 35 USC Sec. 119(f), hereby specifically incorporated by reference in its entirely.

BACKGROUND OF THE INVENTION

The present invention relates to a new and distinct cultivar of *Camellia* plant, botanically known as *Camellia L.* 'Pink Cascade' and will be referred to hereinafter by its cultivar name, 'Pink Cascade'.

'Pink Cascade' was derived from a breeding program by the inventors by applying pollen from a *Camellia parvi-ovata* tree to emasculated flowers of a *Camellia japonica* 'Kuro-tsubaki' tree in the winter of 1996. *Camellia parvi-ovata* is unknown cultivar. Kuro-tsubaki is a Japanese cultivar. It is not patented in China.

'Pink Cascade' differs from one parent *Camellia parvi-ovata* in that the *Camellia parvi-ovata* has white flower color, diameter of flower is 1.0 cm to 1.8 cm, and the length of leave is 4.0 cm to 6.0 cm, and width of leave is 1.5 cm to 2.0 cm, whereas 'Pink Cascade' has light pink flower color, diameter of flower is 2.5 cm to 3.5 cm, the length of leave is 5.0 cm to 8.2 cm, and the width of leave is 1.8 cm to 2.2 cm.

During 1997 to 2001, the seeds derived from the cross were planted and screened until the first flower to obtain favorable seedlings. From 2001 to 2011, the favorable seedlings were propagated by cuttings for five times and the stability tests were carried on before a variety was finally selected and named Pink Cascade in 2011.

Asexual reproduction of the new cultivar was first accomplished by stem cutting from a one year old stem in Shanghai and was further accomplished by same asexual propagation for five generations, and there was no genetic variation, therefore its traits are stable.

SUMMARY OF THE INVENTION

The following traits have been repeatedly observed and are determined to be the characteristics of the new cultivar of *Camellia*. These attributes in combination distinguish 'Pink Cascade' as unique from and all other varieties of *Camellia* known to the Inventors.

1. The shape of leaves of the 'Pink Cascade' is lanceolate.
2. The width of the leaves of 'Pink Cascade' measures at about 1.8 cm to about 2.2 cm, and the length of leaves measures at about 5.0 cm to about 8.2 cm.
3. The plant habit of the 'Pink Cascade' is cascade.

4. The flower stage of the 'Pink Cascade' is about early March to about early April.
5. The flower color of the 'Pink Cascade' is light pink in color.
6. The flower type of the 'Pink Cascade' is single.
7. The diameter of the flowers of the 'Pink Cascade' is about 2 cm to about 4 cm.

'Pink Cascade' can be compared to one parent *Camellia japonica* 'Koro-tsubaki'. Plants of *Camellia japonica* 'Koro-tsubaki' differs from the new *Camellia* 'Pink Cascade' in that the *Camellia japonica* 'Kuro-tsubaki' has straight stem shape, blackish-red flower color, semi-double flower shape, oval leaf shape, and the diameter of *Camellia japonica* 'Kuro-tsubaki' flower is about 6 cm to about 8 cm.

Of the many cultivars known to the present inventors, the most similar in comparison to the new *Camellia* 'Pink Cascade' is the *Camellia* 'Xiao Fenyu' (registered for protection of new varieties of plants in China, registration no. 20120001). Plants of *Camellia* 'Xiao Fenyu' differs from the new *Camellia* 'Pink Cascade' in that *Camellia* 'Xiao Fenyu' has oval leaf shape, straight stem shape, the length of leaf is about 6.5 cm to about 7.5 cm, the width of leaf is about 3 cm to 3.5 cm, and the flower stage is about late February to about April.

BRIEF DESCRIPTION OF THE DRAWINGS

The accompanying colored photographs illustrate the overall appearance and distinct characteristics of the new *Camellia* 'Pink Cascade' showing the colors as true as is reasonably possible with colored reproduction of this type. These photos were taken in 2011 and 2013 in China. Colors in the photographs may differ slightly from the color values cited in the detailed botanical description which accurately describes the color of 'Pink Cascade'.

DETAILED BOTANICAL DESCRIPTION

The following is a detailed description of the new cultivar 'Pink Cascade' as taken from 14-year old plans from stem cutting as grown in Shanghai, China. The phenotype of the new cultivar may vary with variations in environment such as temperature, light intensity, day length, fertilizers and humidity without any change in the genotype of the plant. The description below were taken from 2011 to 2013. The color determination is in accordance with The R.H.S. Colour Chart of The Royal Horticultural Society, London, England, except where general color terms of ordinary dictionary significance are used.

The aforementioned photograph, together with the following observations, measurements and values describe the new *Camellia* 'Pink Cascade' as grown in Shanghai, China. It is planted in the same manner as other common outdoors *Camellia* cultivar, and it grows in area where absolute minimum temperature is above −5° C. 'Pink Cascade' likes warm and humid climate, prefers acidic soil, and grows well in neutral and light alkaline soil.

The range of day-time growing temperatures is the same with other common outdoors *Camellia* cultivar. 'Pink Cascade' grows well in high temperature environment at summer in Shanghai.

The range of night-time growing temperatures is the same with other common outdoors *Camellia* cultivar. The descriptions below were taken from a 14-year old 'Pink Cascade' plant.

General description:

*Blooming season*.—Early March to early April.

Figure 1:
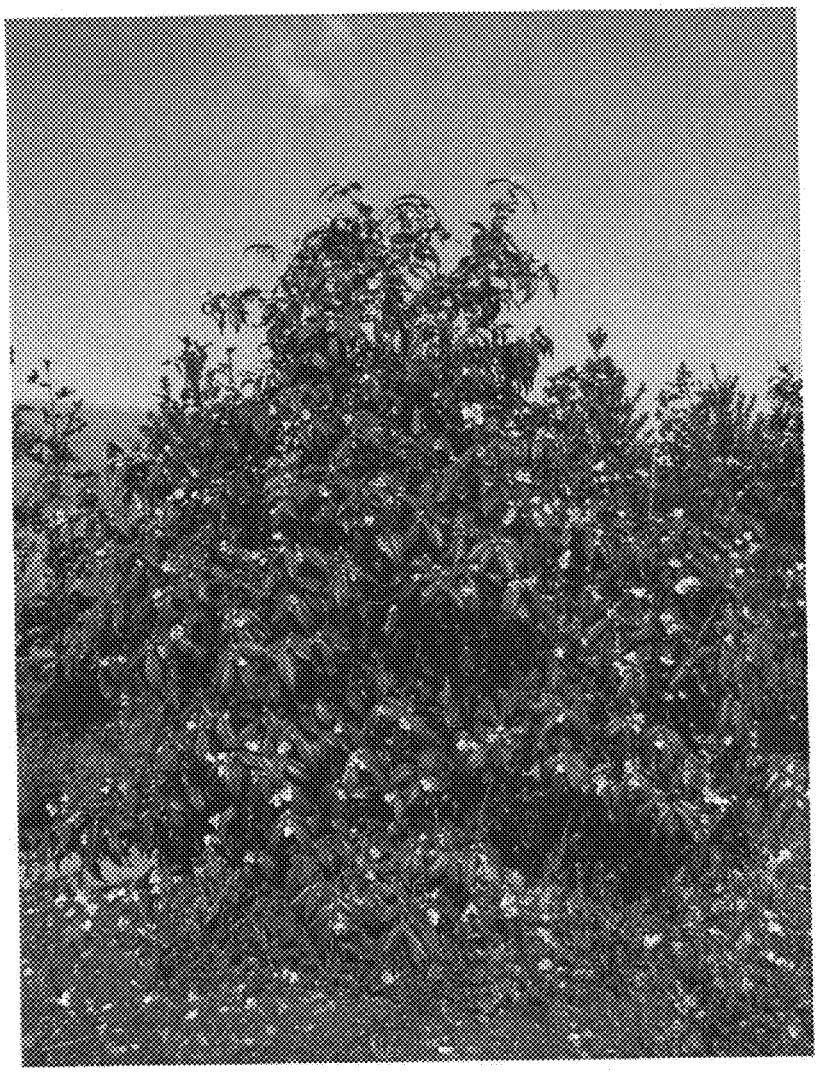
FIG. 1 provides a side view prospective of a typical tree type of seedling which was finally named 'Pink Cascade'. The plant shown in this figure is a 14 years old plant.
Figure 2:
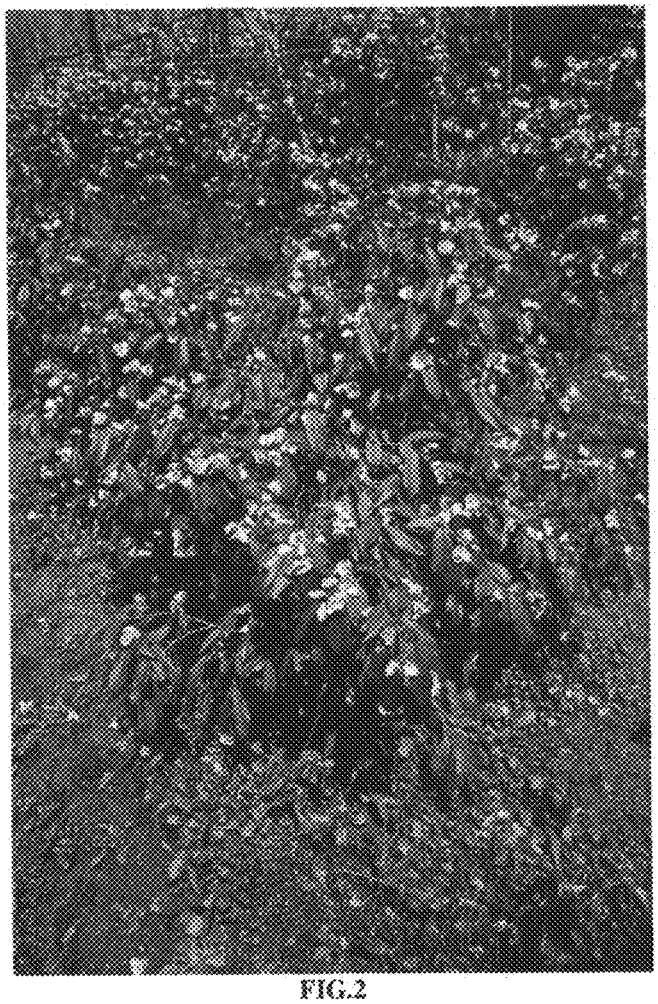
FIG. 2 provides a side view prospective of a typical tree type of 'Pink Cascade' which was propagated by cuttings. The plant shown in this figure is a 8 years old plant.
Figure 5:
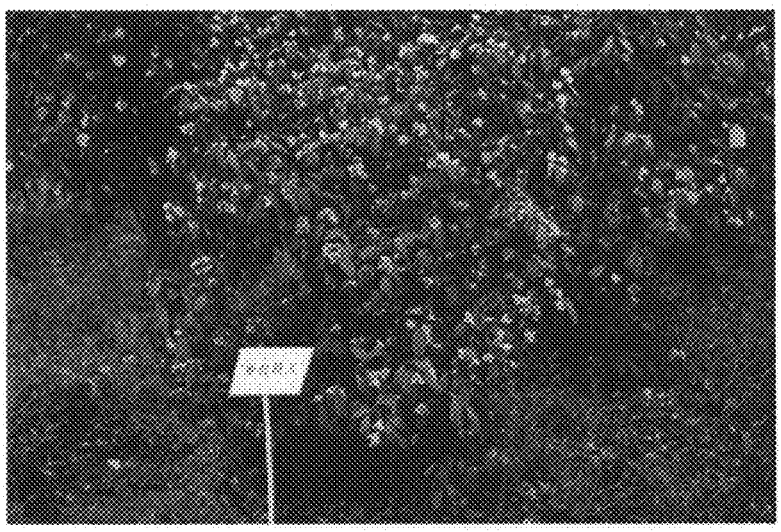
FIG. 5 provides a side view prospective of a 8 years old 'Pink Cascade' plant in flowering stage.

*Plant habit*.—Shrubs (as shown in FIGS. 1, 2 and 5).

*Bark*.—Tan, 197C.

*Plant height*.—About 80 cm.

*Plant diameter, area of spread*.—About 92 cm (FIG. 5, 8-year old plant).

*Winter hardiness and drought/heat tolerance*.—Plant grows at environment temperature ranges from about −5° C. to about 40° C. Drought tolerance is similar to common *Camellia* varieties.

*Disease resistance/susceptibility*.—Sensitive to the mealy bug and anthracnose.

Stem description:

*Color of new stem*.—Tan, 199C.

Figure 3:
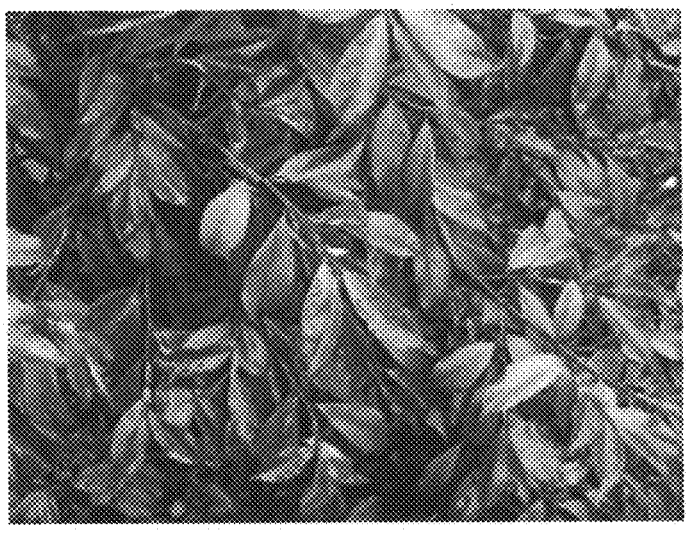
FIG. 3 provides close-up view of the leaves of a 14 years old 'Pink Cascade' plant.

*Stem shape*.—Cascade (as shown in FIG. 3).

*Average length/diameter*.—The average length of main stem is 2-12 cm, the average diameter of main stem is about 2.5 cm, the average number of lateral branch is 2-3, and the average length of lateral branch is 65 cm.

*Average color and texture*.—The RHS color for low lignified young stem is close to 199C, and has pubescence on it. The RHS color for high lignified older stem is close to 197C. Length of Inter node stem is about 0.3-2 cm. (FIG. 5, a 8-year old plant).

Foliage description:

*Leaf color*.—Young leaf: dark purple (FIG. 3); upper surface of young leaf 183A; lower surface of young leaf 183B; vein of young leaf: upper side 144A, lower side 144B. Mature leaf: green to dark green (FIG. 3); upper surface of mature leaf 147A, lower surface of mature leaf 146C; vein of mature leaf 144A.

*Leaf size*.—Mature size: about 5.0 cm to about 8.2 cm in length and about 1.8 cm to about 2.2 cm in width. (FIG. 3).

*Leaf thickness*.—Clusters of alternate leaves arranged almost as a cross, about 3-5 leaves per branch. The leaf thickness is about 0.2 mm to about 0.4 mm.

*Leaf apex*.—Acute (FIG. 3).

*Leaf base*.—Cuneate (FIG. 3).

*Leaf margin*.—Dentate (FIG. 3).

*Leaf shape*.—Lanceolate (FIG. 3).

*Leaf pubescence*.—Absent (FIG. 3).

*Leaf arrangement on stem*.—Clusters (FIG. 3).

*Leaf venation*.—Reticulate. (FIG. 3).

*Leaf texture*.—Smooth.

*Leaf gloss*.—Weak.

Petiole description:

*Length*.—About 3 mm to about 6 mm.

*Diameter*.—About 0.8 mm to about 1.5 mm.

*Color*.—Green, 144E or 178B.

Figure 4:
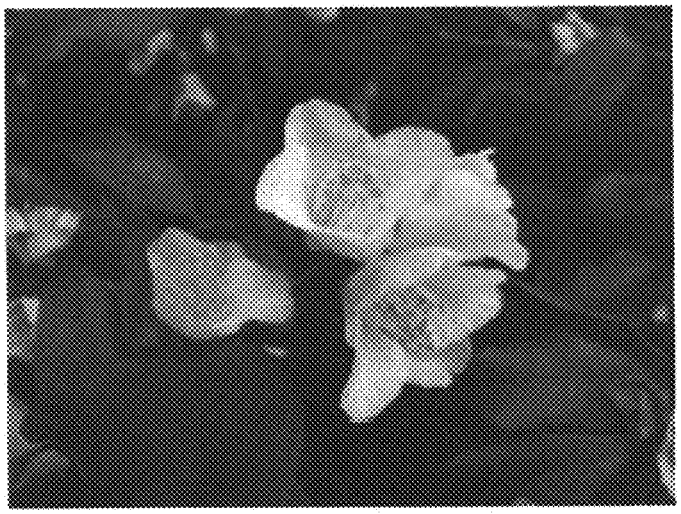
FIG. 4 provides close-up view of the flowers of a 15 years old 'Pink Cascade' plant.

Flower description:

*Inflorescence*.—Number of individual flowers per stem: more than 3 (FIGS. 4 and 5).

*Individual flower*.—Axillary, terminal: some flowers are axillary, and others are terminal. Symmetry: Symmetry (FIG. 4). Fragrance: No fragrance. Diameter: 2.5-3.5 cm. Type: single flower. Flower stage: Early March to early April. Flower buds: the shape of flower bud is oval, and the length before opening is about 15 mm to 24 mm, the diameter is about 7 mm to 11 mm. The RHS color is close to 51A/51B. The length of pedicel is about 1.5 mm to about 3.0 mm, and the diameter is about 2.1 mm to about 3.0 mm. Petals. Number: 5. Size: width of petal is about 12 mm to about 21 mm, and the length is about 21 mm to about 28 mm. The shape of petal base is wide cuneate. Shape: oval (FIG. 4). Apex: concave. Margin: entire. Color: light pink, RHS color close to 52D; when opening: light pink, RHS color close to 52D and 159D. Sepals: Shape: oval. Color: brown, inside surface: close to 178A and 178B; outside surface: close to 144C and 144D. Arrangement: Imbricate structure, about 5 sepals per flower. Width of sepal: about 4 mm to about 8 mm. Length of sepal: about 3 mm to about 9 mm. Stamens Shape: cylindrical. Base: connate. Petaloids: no stamen petaloids have been observed on plants of the new variety of *Camellia*. Average number: about 38-53 basally connate stamens per flower. Size: the length of stamen is about 10 mm to about 20 mm and the diameter is about 0.4 mm to about 0.6 mm. Color: close to 155D. Pistils Stigma: 3-lobed shallow crack. Height: equal or higher than stamens. Pubescence on ovary: absent. Fruits/seeds: Fruit and seeds production have not been observed on plants of the new *Camellia*.

What is claimed is:

1. A new and distinct cultivar of *Camellia* plant named 'Pink Cascade' as herein illustrated and described.

* * * * *

UNITED STATES PATENT AND TRADEMARK OFFICE

CERTIFICATE OF CORRECTION

PATENT NO. : PP26,248 P3
APPLICATION NO. : 13/986736
DATED : December 22, 2015
INVENTOR(S) : Shu-Cheng Feng et al.

It is certified that error appears in the above-identified patent and that said Letters Patent is hereby corrected as shown below:

ON THE TITLE PAGE

Item (12) should read: Shu-Cheng Feng, et al.

Item (72) Inventors should read:

Shu-Cheng Feng, Shanghai, CHINA;
Jian-Guo Fei, Shanghai, CHINA;
Ya-Li Zhang, Shanghai, CHINA; and
Jian-Bin Mo, Shanghai, CHINA.

Item (73) Assignee should read:

Shanghai Botanical Garden, The People's Republic of China, Shanghai (CN)

Signed and Sealed this
Twenty-first Day of June, 2016

Michelle K. Lee

Michelle K. Lee
*Director of the United States Patent and Trademark Office*